(12) United States Patent
Rehwinkel et al.

(10) Patent No.: US 6,914,059 B2
(45) Date of Patent: Jul. 5, 2005

(54) BENZOXAZINE AND BENZOTHIAZINE DERIVATIVES AND THE USE THEREOF IN MEDICAMENTS

(75) Inventors: Hartmut Rehwinkel, Berlin (DE); Peter Hoelscher, Berlin (DE); Stefan Jaroch, Berlin (DE); Detlev Suelzle, Berlin (DE); Margrit Hillmann, Berlin (DE); Gerardine Anne Burton, Berlin (DE); Fiona Mcdonald McDonald, Berlin (DE)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 10/258,016

(22) PCT Filed: Apr. 12, 2001

(86) PCT No.: PCT/EP01/04281
§ 371 (c)(1),
(2), (4) Date: Jul. 23, 2003

(87) PCT Pub. No.: WO01/81323
PCT Pub. Date: Nov. 1, 2001

(65) Prior Publication Data
US 2004/0006075 A1 Jan. 8, 2004

(30) Foreign Application Priority Data
Apr. 19, 2000 (DE) .......................................... 100 20 667

(51) Int. Cl.⁷ .................... C07D 265/36; C07D 279/16; A61K 31/538; A61K 31/5415

(52) U.S. Cl. .................... 514/229.8; 544/105; 544/101; 544/51; 514/230.5

(58) Field of Search ................. 544/105, 101; 514/230.5, 229.8

(56) References Cited

U.S. PATENT DOCUMENTS

| | | |
|---|---|---|
| 6,191,127 B1 | 2/2001 | Holscher et al. |
| 6,365,736 B1 | 4/2002 | Holscher et al. |

FOREIGN PATENT DOCUMENTS

| | | |
|---|---|---|
| WO | WO 9850372 | 11/1998 |
| WO | WO 9912915 | 3/1999 |
| WO | WO 99/41240 | 8/1999 |
| WO | WO 0017173 | 3/2000 |
| WO | WO 0114347 | 3/2001 |

OTHER PUBLICATIONS

M Sudoh, "Identification of a novel inhibitor specific to the Fungal Chitin synthase," J Biol Chem, Aug. 20, 2000, pp. 32901–32905, vol. 275, No. 42, XP000999470, fig 1.

Primary Examiner—James O. Wilson
Assistant Examiner—Kahsay Habte
(74) Attorney, Agent, or Firm—Berlex Inc.

(57) ABSTRACT

Compounds of formula I, their tautomeric and isomeric forms and salts,

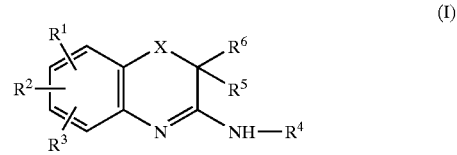

(I)

as well as the process for their production and their use in pharmaceutical agents are described.

10 Claims, No Drawings

BENZOXAZINE AND BENZOTHIAZINE DERIVATIVES AND THE USE THEREOF IN MEDICAMENTS

The invention relates to benzoxazine and benzothiazine derivatives, the process for their production and their use in pharmaceutical agents.

In human cells, there exist at least three forms of nitrogen monoxide synthases, which convert arginine into nitrogen nioxide (NO) and citrulline. Two constitutive NO-synthases (NOS) were identified that are present as calcium/calmodulin-dependent enzymes in the brain (ncNOS or NOS 1) or in the endothelium (ecNOS or NOS 3). Another isoform is the inducible NOS (iNOS or NOS 2), which is a virtually $Ca^{++}$-independent enzyme and is induced after activation of different cells by endotoxin or other substances.

NOS-inhibitors and especially selective inhibitors of NOS 1, NOS 2 or NOS 3 are therefore suitable for treatment of different diseases, which are induced or aggravated by pathological concentrations of NO in cells. A number of reviews provide information on the action and inhibitors of NO-synthases. Mentioned are, for example: Drugs 1, 321 (1998) or Current Pharmac. Design 3, 447 (1997).

As NOS-inhibitors, different compounds are known. For example, arginine derivatives, aminopyridines, cyclic amidine derivatives, phenylimidazoles, etc., are described. It is known from WO 98/50372 and WO 99/12915 that 3-amino-2H-1,4-benzoxazines or 3-amino-2H-1,4-benzothiazines inhibit nitrogen monoxide synthases in a potent and selective manner.

It has now been found that the heterocyclic compounds that are substituted according to the invention, compared to known compounds, have advantages and can be better used as pharmaceutical agents.

The invention relates to the compounds of formula I, their tautomeric and isomeric forms and salts

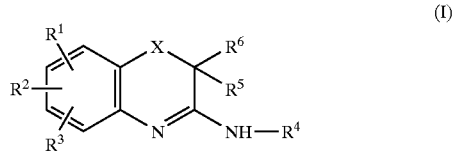

(I)

in which

X means O or S, $R^1$ means —$(CHR^9)_n$—$NR^7$-A-$NR^8$—B or —$(CHR^9)_n$—$NR^7$—B, $R^2$ means hydrogen or $R^1$ and $R^2$ together with two adjacent carbon atoms form a 5-, 6-, 7- or 8-membered ring, which is monocyclic or bicyclic, saturated or unsaturated and in which 1 or 2 $CH_2$ groups can be replaced by oxygen or carbonyl, and which is substituted with $(CHR^9)_r$—$NR^7$-A-$NR^8$—B or —$(CHR^9)_r$—$NR^7$—B and can be substituted with $C_{1-4}$-alkyl, $R^3$ means hydrogen, halogen, $NO_2$, cyano, $CF_3$, —$OCF_3$, —S—$R^9$, —O—$R^9$, $C_{3-7}$-cycloalkyl, —$NR^9$—C(=$NR^{10}$)—$R^{11}$, —NH—CS—$NR^{12}R^{13}$, NH—CO—$NR^{12}R^{13}$, —$SO_2NR^{12}R^{13}$, —CO—$NR^{12}R^{13}$, —CO—$R^{14}$, $NR^{15}R^{16}$, $C_{6-10}$-aryl, which optionally is substituted with halogen, cyano, $C_{1-4}$-alkyl, —S—$R^9$, or —O—$R^9$, 5- or 6-membered heteroaryl with 1 to 4 oxygen, sulfur or nitrogen atoms, $C_{1-6}$-alkyl, which optionally is substituted with halogen, —$OR^9$, —$SR^9$, —$NR^{12}R^{13}$, =$NR^{12}$, =$NOC_{1-6}$-alkyl, =N-NHaryl, phenyl, $C_{3-7}$-cycloalkyl or 5- or 6-membered heteroaryl, $C_{2-6}$-alkenyl, which optionally is substituted with halogen, $CONH_2$, C=N or phenyl, $C_{2-6}$-alkinyl, which optionally is substituted with halogen, $CONH_2$, C=N or phenyl, $R^4$ means hydrogen or acyl, $R^5$ and $R^6$, independently of one another, mean hydrogen, $C_{3-7}$-cycloalkyl, phenyl, $C_{1-6}$-alkyl, $C_{2-6}$-alkenyl or $C_{2-6}$-alkynyl radicals, which can be substituted in each case with halogen, OH, O—$C_{1-6}$-alkyl, SH, S—$C_{1-6}$-alkyl, $NR^{15}R^{16}$, 5- or 6-membered heteroaryl with 1–3 N, O or S atoms, phenyl or $C_{3-7}$-cycloalkyl, $R^7$ means hydrogen, $C_{1-6}$-alkyl, which can be substituted with phenyl, $COOC_{1-6}$-alkyl or $COC_{1-6}$-alkyl, $R^8$ means hydrogen, A means straight-chain or branched —$C_{1-6}$-alkylene, straight-chain or branched —$C_{2-6}$-alkenylene, B means halogenated $C_{1-8}$-alkyl, which can be substituted with —$NHR^7$ or with $C_{6-10}$-aryl, whereby the aryl radical can be substituted with halogen, cyano, OH, $C_{1-4}$-alkoxy, $C_{1-4}$-alkyl, $CF_3$ and —$OCF_3$; $C_{3-8}$-alkinyl, which can be substituted with $C_{6-10}$-aryl; —$(CH_2)_p$—$C_{6-10}$-aryl, which is substituted with —$OCF_3$; or $C_{3-7}$-cycloalkyl, which is substituted with $CF_3$, n and r mean 0, 1 to 6, p means 0 to 6, $R^9$ and $R^{10}$ mean hydrogen or $C_{1-6}$-alkyl, $R^{11}$ means $C_{1-6}$-alkyl, —$NH_2$, —NH—$CH_3$, —NH—CN, $C_{6-10}$-aryl that is optionally substituted with halogen, $C_{1-4}$-alkyl or $CF_3$; or 5- or 6-membered heteroaryl with 1 to 4 nitrogen, sulfur or oxygen atoms that is optionally substituted with halogen, $C_{1-4}$-alkyl or $CF_3$, $R^{12}$ and $R^{13}$ mean hydrogen, $C_{1-6}$-alkyl; phenyl that is optionally substituted with halogen or $C_{1-4}$-alkyl; benzyl that is optionally substituted with halogen or $C_{1-4}$-alkyl; or $C_{3-7}$-cycloalkyl, $R^{14}$ means hydrogen, hydroxy, $C_{1-6}$-alkoxy, phenyl; $C_{1-6}$-alkyl that is optionally substituted with $CO_2H$, $CO_2C_{1-6}$-alkyl, hydroxy, $C_{1-4}$-alkoxy, halogen, $NR^{15}R^{16}$, $CONR^{12}R^{13}$, or phenyl; or $C_{2-6}$-alkenyl that is optionally substituted with phenyl, cyano, $CONR^{12}R^{13}$ or $CO_2C_{1-4}$-alkyl, $R^{15}$ and $R^{16}$ mean hydrogen, $C_{1-6}$-alkyl; phenyl that is optionally substituted with halogen or $C_{1-4}$-alkyl; or benzyl that is optionally substituted with halogen or $C_{1-4}$-alkyl, or $R^{15}$ and $R^{16}$ together with the nitrogen atom form a saturated 5-, 6-, or 7-membered ring, which can contain another nitrogen, oxygen or sulfur atom and can be substituted with $C_{1-4}$-alkyl, or a phenyl, benzyl or benzoyl radical that is optionally substituted with halogen.

The compounds of formula I can be present as tautomers, stereoisomers or geometric isomers. The invention also comprises all possible isomers, such as E- and Z-isomers, S- and R-enantiomers, diastereomers, racemates and mixtures thereof, including the tautomeric compounds of Formulas 1a and 1b

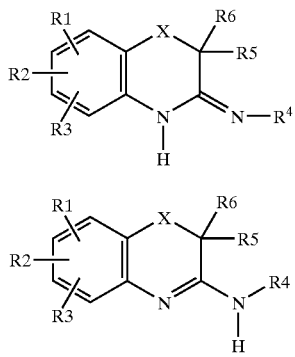

The physiologically compatible salts can be formed with inorganic and organic acids, such as, for example, oxalic acid, lactic acid, citric acid, fumaric acid, acetic acid, maleic acid, tartaric acid, phosphoric acid, HCl, HBr, sulfuric acid, p-toluenesulfonic acid, methanesulfonic acid, i.a.

For salt formation of acid groups, the inorganic or organic bases are also suitable, which are known for the formation of physiologically compatible salts, such as, for example, alkali hydroxides, such as sodium and potassium hydroxide, alkaline-earth hydroxides, such as calcium hydroxide, ammonia, amines such as ethanolamine, diethanolamine, triethanolamine, N-methylglucamine, tris-(hydroxymethyl)-methylamine, etc.

In each case, alkyl means a straight-chain or branched alkyl group, such as, e.g., methyl, ethyl, propyl, isopropyl, n-butyl, sec-butyl, tert-butyl, n-pentyl, sec-pentyl, tert-pentyl, neopentyl, n-hexyl, sec-hexyl, heptyl, or octyl.

If the alkyl radical is substituted with halogen, it can be halogenated in one or more places, and perhalogenated; for example, there can be mentioned fluoromethyl, 2-fluoroethyl, 1-fluoro-prop-2-yl, 4,4,4,-trifluorobutyl, 4,4,4-trifluorobut-2-yl, 2,2,3,3,3-pentafluoropropyl, 3-fluoro-3-phenyl-prop-2-yl, 3-(trifluoromethyl)-cyclohexyl, 2-(trifluoromethyl)-cyclohexyl, 2,2,2-trifluoroethyl, 2,2,3,3,4,4,4-heptafluorobutyl, 3,3,2,2-tetrafluoro-but-1-yl, and 3,3-difluoro-but-1-yl.

Alkenyl and alkynyl substituents are in each case straight-chain or branched and have in particular a double or triple bond. For example, the following radicals can be mentioned: vinyl, 2-propenyl, 1-propenyl, 2-butenyl, 1-butenyl, 3-butenyl, 2-methyl-2-propenyl, ethinyl, 1-propinyl, 2-propinyl, 1-butinyl, 2-butinyl, 2-pentenyl, and 4-hexenyl.

Cycloalkyl is defined respectively as cyclopropyl, cyclobutyl, cyclopentyl, cyclohexyl or cycloheptyl. As a bicyclic compound, for example, bicycloheptane and bicyclooctane can be mentioned.

Halogen means respectively fluorine, chlorine, bromine or iodine.

Aryl is defined respectively as naphthyl or especially phenyl, which can be substituted by the same or a different component in one to three places.

As heteroaryl radicals, which can be bonded via the heteroatom or a carbon atom, for example, the following 5- and 6-ring heteroaromatic compounds can be mentioned:

Imidazole, indole, isooxazole, isothiazole, furan, oxadiazole, oxazole, pyrazine, pyridazine, pyrimidine, pyridine, pyrazole, pyrrole, tetrazole, thiazole, triazole, thiophene, thiadiazole, benzimidazole, benzofuran, benzoxazole, isoquinotine, and quinoline.

In the case of a substitution of the heteroaryl radical, the latter can be substituted by the same or a different component in one to three places.

As a preferred embodiment of $R^{11}$ in the meaning of heteroaryl, thienyl can be considered.

As saturated heterocyclic compounds, for example, piperidine, pyrrolidine, morpholine, thiomorpholine, hexahydroazepine and piperazine can be mentioned. The heterocyclic compound can be substituted by the same or a different component in one to three places with $C_{1-4}$-alkyl or a phenyl, benzyl or benzoyl radical that is optionally substituted with halogen. For example, there can be mentioned: N-methyl-piperazine, 2,6-dimethylmorpholine, phenylpiperazine or 4-(4-fluorobenzoyl)-piperidine.

Simple substitution is preferred for substituents $R^5$ and $R^6$ in 2-position of the oxazine or thiazine, whereby substituent $R^5$ in particular means $C_{1}$-alkyl and $R^6$ is hydrogen.

If $R^1$ and $R^2$ together with two adjacent carbon atoms form a ring, the latter can be in 5,6- or 7,8-position or especially in 6,7-position of the benzoxazine or benzothiazine and has the formula

in which

E means a 3- to 8-membered ring, which is substituted in one to two places with —$(CHR^9)_r$—$NR^7$-A-$NR^8$—B or —$(CHR^9)_r NR^7$—B and optionally is substituted in one to two places with $C_{1-4}$-alkyl and in which 1 or 2 $CH_2$ groups can be replaced by oxygen, carbonyl or its derivatives, and which can be anellated with benzene, such as, for example, indan, and can be present as a bicyclic compound, such as, for example, bicyclooctane.

As structures of E, there can be mentioned, for example:

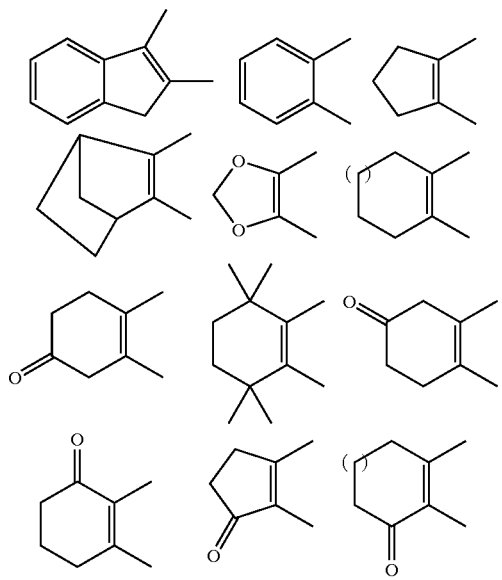

Preferably, two adjacent carbon atoms of the aromatic compound are linked with $C_{1-6}$-alkylene to a 3- to 8-membered ring, especially $C_{3-4}$-alkylene to a 5- to 6-membered ring, which is substituted in any position, but especially in 6-position of the molecule.

Acyl radical $R^4$ is derived from straight-chain or branched aliphatic $C_{1-6}$-carboxylic acids, such as, for example, formic acid, acetic acid, propionic acid, butyric acid, trimethylacetic acid or caproic acid or from known benzenesulfonic acids, which can be substituted with halogen or $C_{1-4}$-alkyl, as well as $C_{1-4}$-alkanesulfonic acids, such as, for example, methanesulfonic acid, and p-toluenesulfonic acid.

Substituent n stands in particular for 1–6.

Other preferred embodiments are:

$R^3$, $R^4$, $R^7$ and $R^9$ in each case mean hydrogen, r means zero,

A means $C_{1-6}$-alkylene, such as methylene, ethylene, propylene, butylene, pentylene or hexylene, $R^1$ means —CH—$R^9)_n$—$NR^7$—B or $R^1$ and $R^2$ together form a 6-membered ring, which is substituted with —CH—$R^9)_r$—$NR^7$—B, B means halogenated alkyl, which can be substituted with —$NHR^7$ or with $C_{6-10}$-aryl, or cyclohexyl, which is substituted with $CF_3$.

The invention also relates to the use of the compounds according to the invention for the production of a pharmaceutical agent for treating diseases that are induced by the action of nitrogen monoxide at pathological concentrations. These include neurodegenerative diseases, inflammatory diseases, auto-immune diseases, and cardiovascular diseases.

For example, there can be mentioned:

Cerebral ischemia, hypoxia and other neurodegenerative diseases, which are brought into contact with inflammations, such as multiple sclerosis, amyotrophic lateral sclerosis and comparable sclerotic diseases, Parkinson's disease, Huntington's disease, Korksakoff's disease, epilepsy, vomiting, sleep disorders, schizophrenia, depression, stress, pain, migraine, hypoglycemia, dementia, such as, e.g., Alzheimer's disease, HIV-dementia and presenile dementia.

They are also suitable for treating diseases of the cardiovascular system and for treating auto-immune and/or inflammatory diseases, such as hypotension, ARDS (adult respiratory distress syndrome), sepsis or septic shock, rheumatoid arthritis, osteoarthritis, insulin-dependent diabetes mellitus (IDDM), inflammatory disease of the pelvis/intestine (bowel disease), meningitis, glomerulonephritis, acute and chronic liver diseases, diseases by rejection (for example allogenic heart, kidney or liver transplants) or inflammatory skin diseases such as psoriasis, etc.

Based on their profile of action, the compounds according to the invention are very well suited for inhibiting the neuronal NOS.

To use the compounds according to the invention as pharmaceutical agents, the latter are brought into the form of a pharmaceutical preparation, which in addition to the active ingredient contains vehicles, adjuvants and/or additives that are suitable for enteral or parenteral administration. The administration can be done orally or sublingually as a solid in the form of capsules or tablets or as a liquid in the form of solutions, suspensions, elixirs, aerosols or emulsions or rectally in the form of suppositories or in the form of injection solutions that can optionally also be administered subcutaneously, intramuscularly or intravenously, or topically or intrathecally. As adjuvants for the desired pharmaceutical agent formulation, the inert organic and inorganic support media that are known to one skilled in the art are suitable, such as, e.g., water, gelatin, gum arabic, lactose, starch, magnesium stearate, talc, vegetable oils, polyalkylene glycols, etc. Moreover, preservatives, stabilizers, wetting agents, emulsifiers or salts for changing the osmotic pressure or buffers can optionally be contained.

For parenteral administration, especially injection solutions or suspensions, especially aqueous solutions of the active compounds in polyhydroxyethoxylated castor oil, are suitable.

As vehicle systems, surface-active adjuvants such as salts of bile acids or animal or plant phospholipids, but also mixtures thereof as well as liposomes or their components can also be used.

For oral administration, especially tablets, coated tablets or capsules with talc and/or hydrocarbon vehicles or binders, such as, for example, lactose, corn or potato starch, are suitable. The administration can also be done in liquid form, such as, for example, as a juice, to which optionally a sweetener is added.

The dosage of the active ingredients can vary depending on method of administration, age and weight of the patient, type and severity of the disease that is to be treated and similar factors. The daily dose is 1–2000 mg, preferably 20–500 mg, whereby the dose can be given as an individual dose to be administered one time or divided into two or more daily doses.

The NOS-inhibitory action of the compounds of formula I and their physiologically compatible salts can be determined according to the methods by Bredt and Snyder in Proc. Natl. Acad. Sci. USA 86, 9030 (1989).

The production of the compounds according to the invention is carried out in that a compound of formula II or its salt

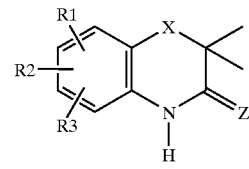

IIa oder

[Key: oder = or]

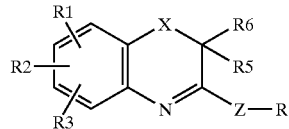

IIb in which $R^1$, $R^2$, $R^3$, $R^5$, $R^6$ and X have the above-mentioned meaning, Z is oxygen or sulfur and R means $C_{1-6}$-alkyl, is reacted with ammonia or primary amines, whereby existing amino groups are optionally intermediately protected and optionally then acylated, the isomers are separated or the salts are formed.

The reaction with ammonia is possible under pressure in autoclaves with excess ammonia at low temperatures (−78° C.) or by stirring in methanol that is saturated with ammonia at room temperature. Thiolactams are preferably reacted. If the reaction is with amines, first the iminoethers or iminothioethers are produced from lactam or thiolactam as intermediate compounds (e.g., with methyl iodide or dimethyl sulfate), and the latter are reacted with or without isolation of the intermediate compounds with the corresponding amines or their salts.

As amino protective groups, for example, carbamates, such as tert-butyloxycarbonyl, benzyloxy-carbonyl or acetyl, are suitable.

In the precursor stages, optionally sulfides are oxidized, esters are saponified, acids are esterified, hydroxy groups are etherified or acylated, amines are acylated, alkylated, diazotized, halogenated, $NO_2$ is introduced or reduced, reacted with isocyanates or isothiocyanates, the isomers are separated or the salts are formed.

The saponification of an ester group can be done basically or acidically by hydrolysis being performed at room temperature or at an elevated temperature up to the boiling point of the reaction mixture in the presence of alkali hydroxides in ethanol or other alcohols or with use of acids, such as, e.g., hydrochloric acid, and optionally salts of aminobenzoxazines or -thiazines being further processed.

The esterification of carboxylic acid is done in a way that is known in the art with diazomethane or the corresponding alcohol in acid or in the presence of an activated acid derivative. As activated acid derivatives, for example, acid chloride, acid imidazolide or acid anhydride are suitable.

The reduction of an ester group to alcohol is carried out in a way that is known in the art with DIBAH in suitable solvents at low temperatures. The reductive amination of a ketone or a benzaldehyde with amine while adding boron hydride provides the corresponding amines. With suitably selected diamines, symmetrical or unsymmetrical amino compounds are obtained after identical or different aldehydes or ketones are added.

In addition, a nitro group or halogen, especially bromine, can be introduced by electrophilic, aromatic substitution. Mixtures that are produced in this case can be separated in the usual way, also using HPLC. If a nitrile is present, the latter can be saponified according to known processes or can be converted into the corresponding amine, tetrazole or amidoxime, or it is in a substituted amidine by attacking substituted anilines or amines.

The Friedel-Crafts acylation is used successfully in lactams of type IIa, and then the lactam can be converted selectively into the thiolactam, or the acylation product can be reductively aminated.

The reduction of the nitro group or optionally the cyano group to the amino group is carried out catalytically in polar solvents at room temperature or at an elevated temperature under hydrogen pressure. As catalysts, metals such as Raney nickel or noble metal catalysts such as palladium or platinum optionally in the presence of barium sulfate or on vehicles are suitable. Instead of hydrogen, ammonium formate or formic acid can also be used in a known way. Reducing agents such as tin(II) chloride can also be used, such as complex metal hydrides optionally in the presence of heavy metal salts. The ester group can be advantageously introduced before the reduction as in Formula V. For nitro groups, reduction with zinc or iron in acetic acid has proven its value.

If a single or multiple alkylation of an amino group or a CH-acid carbon position is desired, alkylation can be performed with, for example, alkyl halides according to commonly used methods. Protection of the lactam group as an anion by a second equivalent base or by a suitable protective group optionally is necessary.

The acylation of the amino group is carried out in the usual way with, for example, an acid halide or acid anhydride, optionally in the presence of a base.

The introduction of the halogens chlorine, bromine or iodine via the amino group can also be carried out, for example, according to Sandmeyer, by the diazonium salts that are formed intermediately with nitrites being reacted with Cu(I) chloride or Cu(I) bromide in the presence of the corresponding acids such as hydrochloric acid or hydrobromic acid or being reacted with potassium iodide.

Benzyl alcohols can be converted into corresponding mesylates or benzyl halides as usual with methanesulfonyl chloride.

The introduction of an $NO_2$ group is possible by a number of known nitration methods. For example, nitration can be performed with nitrates or with nitronium tetrafluoroborate in inert solvents, such as halogenated hydrocarbons or in sulfolane or glacial acetic acid. Introduction by, e.g., nitrating acid in water or concentrated sulfric acid as a solvent is also possible at temperatures of between $-10°$ C. and $30°$ C.

The isomer mixtures can be separated into enantiomers or E/Z-isomers according to commonly used methods, such as, for example, crystallization, chromatography or salt formation. The enantiomers or enantiomer-pure diastereomers can also be obtained by chromatography on chiral phases as well as by stereoselective syntheses.

The production of the salts is carried out in the usual way, by a solution of the compound of Formula I—optionally also with protected amino groups—being mixed with the equivalent amount of acid or excess acid, which optionally is in solution, and the precipitate being separated or the solution being worked up in the usual way.

Nucleophilic substitution of benzyl halides with secondary amines yields the corresponding benzylamines.

Thiolactams of formula IIa (Z=S) are obtained from, for example, lactams with phosphorus pentasulfide $P_4S_{10}$) or Lawesson's reagent (2,4-bis(4-methoxyphenyl)-1,3,2,4-dithiaphosphetane-2,4-disulfide) in suitable solvents, and compounds of Formula IIb can be obtained by, for example, reaction with Meerwein reagent (trimethyloxonium tetrafluoroborate).

The invention also relates to the intermediate compounds of Formulas IIa and IIb and salts thereof

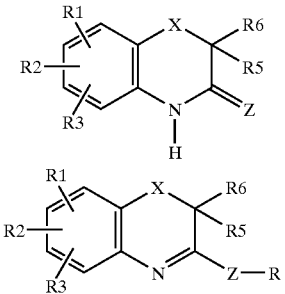

in which
$R^1$, $R^2$, $R^3$, $R^5$, $R^6$ and X have the above-mentioned meaning, Z is oxygen or sulfur, and R means $C_{1-6}$-alkyl.

The production of pharmacologically active compounds from the intermediate products is carried out as described above.

The production of the compounds of Formula Ia can be carried out, for example, in that a compound of Formula III

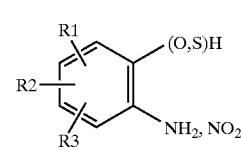

in which $R^1$ to $R^3$ have the above-mentioned meaning, is reacted with a compound of Formula IV

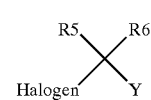

in which $R^5$ and $R^6$ have the above-mentioned meaning, and Y is a reactive carboxyl group such as acid halide, nitrile, carboxylic acid ester, and optionally is reductively cyclized, or in that a compound of Formula V

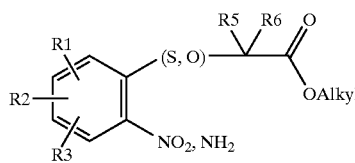

is reductively cyclized.

Aromatic thiols of type III are obtained, i.a., as described in Chem. Pharm. Bull. 39, 2888 (1991) and the literature that is mentioned there by rearrangement of the corresponding dimethylaminothiocarbamates.

The introduction of substituents $R^1$ to $R^3$ can be carried out in the stage of the compounds of Formula III or II.

For the production of compounds of Formula II, the aldehyde or the ketone of the corresponding 1,4-benzoxazin-3-one or 1,4-benzothiazin-3(4H)-one can be reductively aminated. This can also be done in two places with suitably selected diamines. Diamines can also be reacted with the aldehyde of 1,4-benzoxazin-3-one and simultaneously with other suitably selected aldehydes. If the introduction of a heteroaryl radical Q is desired, the corresponding halogen derivative can be substituted nucleophilically with amine. If a primary or secondary amino group is present, it may be advantageous to protect the latter intermediately, for example by introduction of a tert-butoxycarbonyl group, which is cleaved in the usual way after the amidine formation.

Monoacylated diamines are also obtained, as described in the literature (Synthesis 11, 917 (1988)), by reaction of benzamides with diamine with release of ammonia.

If the production of the starting compounds is not described, the latter are known and commercially available or can be produced analogously to known compounds or according to processes that are described here.

New compounds were identified by one or more of the following methods: melting point, mass spectroscopy, NMR. NMR spectra were measured with a Bruker 300 MHz device; the (deuterated) solvents are abbreviated as follows: $CDCl_3$ (chloroform), DMSO (dimethyl sulfoxide). Alterations are indicated in delta and ppm. Here: m means multiplet, several signals; s means singlet; d means doublet; dd means double doublet; t means triplet; q means quartet; H means hydrogen protons; J means coupling constant. In addition, THF means tetrahydrofuran, DMF means N,N-dimethylformamide, MeOH means methanol, EE means ethyl acetate, ml means milliliter, RT means room temperature. All solvents are p.A. grade, unless otherwise indicated. All reactions are performed under protective gas, unless these are aqueous solutions.

Below, the production of several precursors, intermediate products and products is described by way of example.

EXAMPLE 1

(2R)-Methyl-3-amino-6-(2,2,3,3,3-pentafluoropropylamino-methyl)-2H-1,4-benzoxazine-dihydrochloride a) (2R)-Methyl-3-oxo-6-(2,2,3,3,3-pentafluoropropylamino-methyl)-3,4-dihydro-2H-1,4-benzoxazine 1.15 g (5.98 mmol) of (2R)-methyl-3'-oxo-6-aminomethyl-2H-1,4-benzoxazine, 885.7 mg (5.98 mmol) of pentafluoropropionaldehyde, 11.4 mg (0.06 mmol) of para-toluenesulfonic acid and 20 ml of benzene are heated for seven hours in a water separator. After cooling, it is spun in until a dry state is reached, and the residue is chromatographed on silica gel (mobile solvent: ethyl acetate/hexane). 712 mg (37%) of the desired compound is obtained.

MS (Cl) m/e (relative intensity) 340 ($MNH_4^+$, 78), 193 (96), 176(100)

b) (2R)-Methyl-3-oxo-6-(2,2,3,3,3-pentafluoropropylamino-methyl)-3,4-dihydro-2H-1,4-benzoxazine 712 mg (2.21 mmol) of (2R)-methyl-3-oxo-6-(2,2,3,3,3,-pentafluoropropylimino-methyl-3,4-dihydro-2H-1,4-benzoxazine is dissolved in 30 ml of methanol and mixed with 83.6 mg (2.21 mmol) of sodium borohydride. After stirring overnight at room temperature, the batch is added to water and shaken three times with ethyl acetate. The combined organic phases are washed with saturated sodium chloride solution, dried and spun in. After chromatography on silica gel (mobile solvent: ethyl acetate/hexane), 396.7 mg (55%) of the desired compound is obtained.

MS (Cl) m/e (relative intensity) 325 ($M^+$, 77.5), 193 (86), 176 (100)

c) (2R)-Methyl-3-thioxo-6-(2,2,3,3,3-pentafluoropropylamino-methyl)-3,4-dihydro-2H-1,4-benzoxazine 396 mg (1.22 mmol) of (2R)-methyl-3-oxo-6-(2,2,3,3,3-pentafluoropropylamino-methyl)-3,4-dihydro-2H-1,4-benzoxazine is mixed in 40 ml of dimethoxymethane with 496 mg (1.22 mmol) of Lawesson's reagent and stirred overnight at room temperature. After the solvent is spun off, the residue is chromatographed (mobile solvent: ethyl acetate/hexane). 234.5 mg (54%) of the desired thiolactam is isolated.

MS (Cl) m/e (relative intensity) 341 ($M^+$, 54.5), 309 (100), 209 (58.3), 192 (94)

d) (2R)-Methyl-3-amino-6-(2,2,3,3,3-pentafluoropropylamino-methyl)-2H-1,4-benzoxazine Dihydrochloride 234 mg (0.658 mmol) of (2R)-methyl-3-thioxo-6-(2,2,3,3,3-pentafluoropropylamino-methyl)-3,4-dihydro-2H-1,4-benzoxazine is stirred with 10 ml of a 7M solution of ammonia in methanol for two hours at room temperature. Then, the batch is evaporated to the dry state, and the residue is dissolved in dichloromethane. After 3 ml of a 4M solution of hydrochloric acid in dioxane is added, the batch is mixed with 20 ml of methyl-tert-butyl ether and stirred for two hours at room temperature. The amount of precipitated product is 168.7 mg (65%).

MS (Cl) m/e (relative intensity) 324 ($M^+$, 100), 192 (12.5), 172 (28.5)

With use of the corresponding starting materials, the following are synthesized analogously:

(2R)-Methyl-3-amino-6-(2,2,2-trifluoroethylamino-methyl)-2H-1,4-benzoxazine-dihydrochloride (2R)-methyl-3-amino-6-(2,2,3,3,3-pentafluoropropylamino-ethyl)-2H-1,4-benzoxazine-dihydrochloride, (2R)-methyl-3-amino-6-(2,2,2-trifluoroethylamino-ethyl)-2H-1,4-benzoxazine-dihydrochloride, (2R)-methyl-3-amino-6-(2,2,3,3,4,4,4-heptafluorobutylamino-ethyl)-2H-1,4-benzoxazine-dihydrochloride.

EXAMPLE 2

(2R)-Methyl-3-amino-6-(4,4,4-trifluorobutylamino-methyl)-2H-1,4-benzoxazine-dihydrochloride a) (2R)-Methyl-3-oxo-6-(4,4,4-trifluorobutylamino-methyl)-3,4-dihydro-2H-1,4-benzoxazine 780 mg (3.668 mmol) of (2R)-methyl-3-oxo-6-aminomethyl-2H-1,4-benzoxazine-hydrochloride, 462.4 mg (3.668 mmol) of 4,4,4-trifluorobutyraldehyde and 371.2 mg (3.668 mmol) of triethylamine are dissolved in a mixture that consists of methanol and tetrahydrofuran (4:1). After three hours of stirring at room temperature, 75.2 mg of sodium borohydride is added. After stirring overnight at room temperature, the batch is added to water and shaken three times with ethyl acetate. The combined organic phases are washed with saturated sodium chloride solution, dried and spun in. After chromatography on silica gel (mobile solvent: dichloromethane/isopropanol, 608.8 mg (55%) of the desired compound is obtained.

MS (CI) m/e (relative intensity) 303 (M+, 100)

According to the method that is described here, the following compounds are produced from the 2-methyl-6-keto-6,7,8,9-tetrahydro-2H-naphth[2,3-b]-1,4-oxazin-3-one and 6-formyl-2-methyl-2H-1,4-benzoxazin-3(4H)-one described in WO99/12915 by reductive amination with the corresponding amines:

(2R)-Methyl-3-oxo-6-([4-amino-3,3,2,2-tetrafluoro-butyl-1-amino]-methyl)-2H-1,4-benzoxazine (2R)-methyl-3-oxo-6-([4-amino-3,3-difluoro-butyl-1-amino]-methyl)-2H-1,4-benzoxazine (6S)-(2R)-methyl-6-(4,4,4-trifluorobutyl amino)-6,7,8,9-tetrahydro-2H-naphth[2,3-b]-1,4-oxazin-3-one and (6R)-(2R)-methyl-6-(4,4,4-trifluorobutyl-amino)-6,7,8,9-tetrahydro-2H-naphth[2,3-b]-1,4-oxazin-3-one and (6S)-(2S)-methyl-6-(4,4,4-trifluorobutyl-amino)-6,7,8,9-tetrahydro-2H-naphth[2,3-b]-1,4-oxazin-3-one and (6R)-(2S)-methyl-6-(4,4,4-trifluorobutyl-amino)-6,7,8,9-tetrahydro-2H-naphth[2,3-b]-1,4-oxazin-3-one b) (2R)-Methyl-3-oxo-6-(4,4,4-trifluorobutyl-tert-butyloxycarbonyl-amino-methyl)-3,4-dihydro-2H-1,4-benzoxazine 608 mg (2.014 mmol) of (2R)-methyl-3-oxo-6-(4,4,4-trifluorobutylamino-methyl)-3,4-dihydro-2H-1,4-benzoxazine is stirred with 439.9 mg (2.014 mmol) of di-tert-butyldicarbonate and 303 mg (2.995 mmol) of triethylamine in 15 ml of dichloromethane for four hours at room temperature. The batch is spun in until a dry state is reached, and the residue is put on a column on silica gel (mobile solvent: ethyl acetate/hexane). 727.6 mg (99%) of the desired compound is isolated.

MS (CI) m/e (relative intensity) 420 ($MNH_4^+$, 6.5), 403 ($M^+$, 1I), 364 (100), 303 (44), 176 (27)

Synthesized analogously are:

(2R)-Methyl-3-oxo-6-([4-tert-butyloxycarbonyl-amino-3,3,2,2-tetrafluoro-butyl-1-tert-butyloxycarbonyl-amino]-methyl)-2H-1,4-benzoxazine (2R)-methyl-3-oxo-6-([4-tert-butyloxycarbonyl-amino-3,3-difluoro-butyl-1-tert-butyloxycarbonyl-amino]-methyl)-2H-1,4-benzoxazine (6S)-(2R)-methyl-6-(4,4,4-trifluorobutyl tert-butyloxycarbonyl-amino)-6,7,8,9-tetrahydro-2H-naphth[2,3-b]-1,4-oxazin-3-one and (6R)-(2R)-methyl-6-(4,4,4-trifluorobutyl-tert-butyloxycarbonyl-amino)-6,7,8,9-tetrahydro-2H-naphth[2,3-b]-1,4-oxazin-3-one and (6S)-(2S)-methyl-6-(4,4,4-trifluorobutyl-tert-butyloxycarbonyl-amino)-6,7,8,9-tetrahydro-2H-naphth[2,3-b]-1,4-oxazin-3-one and (6R)-(2S)-methyl-6-(4,4,4-trifluorobutyl-tert-butyloxycarbonyl-amino)-6,7,8,9-tetrahydro-2H-naphth[2,3-b]-1,4-oxazin-3-one c) (2R)-Methyl-3-thioxo-6-(4,4,4-trifluorobutyl-tert-butyloxycarbonyl-amino-methyl]-3,4-dihydro-2H-1,4-benzoxazine 727 mg, (1.986 mmol) of (2R)-methyl-3-oxo-6-(4,4,4-trifluorobutyl-tert-butyloxycarbonyl-amino-methyl)-3,4-dihydro-2H-1,4-benzoxazine is mixed in 7 ml of dimethoxyethane with 802.7 g of Lawesson's reagent and stirred overnight at room temperature. After the solvent is spun off, the residue is chromatographed (mobile solvent: ethyl acetate/hexane). 744 mg (98%) of the desired thiolactam is isolated.

MS (FAB) m/e (relative intensity) 419 ($M^+$, 36.5), 217 (56), 109 (35), 91 (100)

Synthesized analogously are:

(2R)-Methyl-3-thioxo-6-([4-tert-butyloxycarbonyl-amino-3,3,2,2-tetrafluoro-butyl-1-tert-butyloxycarbonyl-amino]-methyl)-2H-1,4-benzoxazine (2R)-methyl-3-thioxo-6-([4-tert-butyloxycarbonyl-amino-3,3-difluoro-butyl-1-tert-butyloxycarbonyl-amino-]-methyl)-2H-1,4-benzoxazine (6S)-(2R)-methyl-6-(4,4,4-trifluorobutyl tert-butyloxycarbonyl-amino)-6,7,8,9-tetrahydro-2H-naphth[2,3-b]-1,4-oxazine-3-thione and (6R)-(2R)-methyl-6-(4,4,4-trifluorobutyl-tert-butyloxycarbonyl-amino)-6,7,8,9-tetrahydro,-2H-naphth[2,3-b]-1,4-oxazine-3-thione and (6S)-(2S)-methyl-6-(4,4,4-trifluorobutyl-tert-butyloxycarbonyl-amino)-6,7,8,9-tetrahydro-2H-naphth[2,3-b]-1,4-oxazine-3-thione and (6R)-(2S)-methyl-6-(4,4,4-trifluorobutyl-tert-butyloxycarbonyl-amino)-6,7,8,9-tetrahydro-2H-naphth[2,3-b]-1,4-oxazine-3-thione d) (2R)-Methyl-3-amino-6-(4,4,4-trifluorobutyl-tert-butyloxycarbonyl-amino-methyl)-2H-1,4-benzoxazine 744 mg (1.946 mmol) of (2R)-methyl-3-thioxo-6-(4,4,4-trifluorobutyl-tert-butyloxycarbonyl-amino-methyl)-3,4-dihydro-2H-1,4-benzoxazine is mixed with 10 ml of a 7M solution of ammonia in methanol and stirred overnight at room temperature. The batch is spun in until a dry state is reached, and the residue is chromatographed on silica gel (mobile solvent: dichloromethane/isopropanol). 643.7 mg (85%) of the desired compound is isolated.

MS (CI) m/e (relative intensity) 402 ($M^+$, 100)

Synthesized analogously are:

(2R)-Methyl-3-amino-6-([4-tert-butyloxycarbonyl-amino-3,3,2,2-tetrafluoro-butyl-1-tert-butyloxycarbonyl-amino]-methyl)-2H-1,4-benzoxazine (2R)-methyl-3-amino-6-{[4-tert-butyloxycarbonyl-amino-3,3-difluoro-butyl-1-tert-butyloxycarbonyl-amino]-methyl)-2H-1,4-benzoxazine (6S)-(2R)-methyl-6-(4,4,4-trifluorobutyl-tert-butyloxycarbonyl-amino)-6,7,8,9-tetrahydro-2H-naphth[2,3-b]-1,4-oxazine-3-amine and (6R)-(2R)-methyl-6-(4,4,4-trifluorobutyl-tert-butyloxycarbonyl-amino)-6,7,8,9-tetrahydro-2H-naphth[2,3-b]-1,4-oxazine-3-amine and (6S)-(2S)-methyl-6-(4,4,4-trifluorobutyl-tert-butyloxycarbonyl-amino)-6,7,8,9-tetrahydro-2H-naphth[2,3-b]-1,4-oxazine-3-amine and (6R)-(2S)-methyl-6-(4,4,4-trifluorobutyl-tert-butyloxycarbonyl-amino)-6,7,8,9-tetrahydro-2H-naphth[2,3-b]-1,4-oxazine-3-amine e) (2R)-Methyl-3-amino-6-(4,4,4-trifluorobutylamino-methyl)-2H-1,4-benzoxazine-dihydrochloride 643 mg (1485 mmol) of (2R)-methyl-3-amino-6-(4,4,4-trifluorobutyl-tert-butyloxycarbonyl-amino-methyl)-2H-1,4-benzoxazine is dissolved in 5 ml of dioxane and mixed with 5 ml of a 4M solution of hydrochloric acid in dioxane. After being stirred overnight, the batch is spun in until a dry state is reached, and the residue is absorptively precipitated with a mixture that consists of dichloromethane/methyl-tert-butyl ether (1:1). After being suctioned off, the compound that is obtained is dried by the oil pump.

MS (Cl) m/e (relative intensity) 302 (M$^+$, 100), 175 (19.5), 128 (20.3)

With use of the corresponding starting materials, the following are synthesized analogously:

(2R)-Methyl-3-amino-6-(4,4,4-trifluorobutylamino-ethyl)-2H-1,4-benzoxazine-dihydrochloride (2R)-methyl-3-amino-6-(2-fluoroethylamino-methyl)-2H-1,4-benzoxazine-dihydrochloride Synthesized analogously are:

(2R)-Methyl-3-amino-6-([4-amino-3,3,2,2-tetrafluoro-butyl-1-amino]-methyl)-2H-1,4-benzoxazine-trihydrochloride (2R)-methyl-3-amino-6-([4-amino-3,3-difluoro-butyl-1-amino]-methyl)-2H-1,4-benzoxazine-trihydrochloride (6S)-(2R)-methyl-6-(4,4,4-trifluorobutylamino)-6,7,8,9-tetrahydro-2H-naphth[2,3-b]-1,4-oxazine-3-amine-dihydrochloride and (6R)-(2R)-methyl-6-(4,4,4-trifluorobutylamino)-6,7,8,9-tetrahydro-2H-naphth[2,3-b]-1,4-oxazine-3-amine-dihydro chloride and (6S)-(2S)-methyl-6-(4,44-trifluorobutylamino)-6,7,8,9-tetrahydro-2H-naphth[2,3-b]-1,4-oxazine-3-amine dihydrochloride and (6R)-(2S)-methyl-6-(4,4,4-trifluorobutylamino)-6,7,8,9-tetrahydro-2H-naphth[2,3-b]-1,4-oxazine-3-amine dihydrochloride

EXAMPLE 3

(2R)-Methyl-3-amino-6-[4,4,4-trifluorobut-(2RS)-yl-amino-methyl]-2H-1,4-benzoxazine-dihydrochloride a) (2R)-Methyl-3-oxo-6-[4,4,4-trifluorobut-(2RS)-yl-amino-methyl]-3,4-dihydro-2H-1,4-benzoxazine 427.7 mg (2.615 mmol) of racemic 4,4,4-trifluoro-but-2-yl-amine-hydrochloride, produced according to K. -R. Gassen and W. Kimse, Chem. Ber. 119, 2233 (1986), is dissolved in a mixture that consists of methanol and tetrahydrofuran (4:1). After 264.6 mg (2.615 mmol) of triethylamine is added, it is stirred for one-half hour at room temperature. Then, 500 mg (2.615 mmol) of (2R)-methyl-3'-oxo-6-formyl-2H-1,4-benzoxazine is added, and it is stirred for 15 hours at room temperature. After 54.4 mg (1.438 mmol) of sodium borohydride is added, the batch is stirred for five days. Since starting material is also always still present after this time, 54.4 mg (1.438 mmol) of sodium borohydride is added again. After another 18 hours at room temperature, the batch is added to water/brine and extracted three times with ethyl acetate. The combined organic phases are washed with saturated sodium chloride solution, dried and spun in. After chromatography on silica gel (mobile solvent: dichloromethane/ethanol/ammonia water), 581.6 mg (74%) of the desired compound is obtained as a diastereomer mixture.

MS (Cl) m/e (relative intensity) 303 (M$^+$, 100), 176 (55)

b) (2R)-Methyl-3-oxo-6-[4,4,4-trifluorobut-(2RS)-yl-tert-butyloxycarbonyl-amino-methyl]-3,4-dihydro-2H-1,4-benzoxazine 580 mg (1.918 mmol) of (2R)-methyl-3-oxo-6-[4,4,4-trifluorobut-(2RS)-yl-amino-methyl]-3,4-dihydro-2H-1,4-benzoxazine is stirred with 502.3 mg (2.302 mmol) of di-tert-butyl dicarbonate and 291.1 mg (2.877 mmol) of triethylamine in 11 ml of dichloromethane for 20 hours at room temperature. The batch is diluted with 200 ml of dichloromethane and shaken with saturated sodium bicarbonate solution and with brine. The organic phase is spun off after drying, and the residue is put on a column on silica gel (mobile solvent: ethyl acetate/hexane). 751.8 mg (97%) of the desired compound is isolated as a diastereomer mixture.

MS (Cl) m/e (relative intensity) 403 (M$^+$, 9), 364 (100), 347 (75.8), 303 (30.5), 176 (69.5)

c) (2R)-Methyl-3-thioxo-6-[4,44-trifluorobut-(2RS)-yl-tert-butyloxycarbonyl-amino-methyl]-3,4-dihydro-2H-1,4-benzoxazine 750 mg (1.864 mmol) of (2R)-methyl-3'-oxo-6-[4,4,4-trifluorobut-(2RS)-yl-tert-butyloxycarbonyl-amino-methyl]-3,4-dihydro-2H-1,4-benzoxazine is mixed in 29 ml of dimethoxyethane with 829.3 mg (2.05 mmol) of Lawesson's reagent and stirred overnight at room temperature. The batch is filtered, and the filter residue is washed with dichloromethane. After the solvent is spun off, the residue is chromatographed (mobile solvent: ethyl acetate/hexane). 754.2 mg (97%) of the desired thiolactam is isolated as a diastereomer mixture.

MS (Cl) m/e (relative intensity) 419 (M$^+$, 21), 363 (100)

d) (2R)-Methyl-3'-amino-6-[4,4,4-trifluorobut-(2RS)-yl-tert-butyloxycarbonyl-amino-methyl]-2H-1,4-benzoxazine 754 mg (1.802 mmol) of (2R)-methyl-3-thioxo-6-[4,4,4-trifluorobut-(2RS)-yl-tert-butyloxycarbonyl-amino-methyl]-3,4-dihydro-2H-1,4-benzoxazine is mixed with 29 ml of a 7 M solution of ammonia in methanol and stirred for two hours at room temperature. The batch is mixed with 20 ml of toluene and spun in until a dry state is reached. The residue is chromatographed on silica gel (mobile solvent: dichloromethane/isopropanol/ammonia water). 553.5 mg (77%) of the desired compound is isolated as a diastereomer mixture.

MS (Cl) m/e (relative intensity) 402 (M$^+$, 100), 345 (29.8)

e) (2R)-Methyl-3-amino-6-[4,4,4-trifluorobut-(2RS)-yl-amino-methyl]-2H-1,4-benzoxazine-dihydrochloride 550 mg (1.37 mmol) of (2R)-methyl-3-amino-6-[4,4,4-trifluorobut-(2RS)-yl-tert-butyloxycarbonyl-amino-methyl]-2H-1,4-benzoxazine is dissolved in 3 ml of dioxane and mixed with 4 ml of a 4 M solution of hydrochloric acid in dioxane. After another half-hour of stirring at room temperature, a semicrystalline precipitate begins to separate. After three hours, the supernatant solvent is decanted, and 20 ml of toluene is added. After the toluene is spun in, the residue is dried at the oil pump. 379 mg (74%) of the desired compound is isolated as a diastereomer mixture.

MS (Cl) m/e (relative intensity) 302 (M$^+$, 100), 175 (89.5)

EXAMPLE 4

(2R)-Methyl-3-amino-6-[(3R)-fluoro-3-phenyl-prop-(2R)-yl-amino-methyl]-2H-1,4-benzoxazine-dihydrochloride a) [(1S)-Phenyl-(2R)-(2,5-dimethylpyrrol-1-yl)]-propan-1-ol 3.97 g (26.257 mmol) of (1S,2R)-(+)-norephedrine is refluxed for four hours with 3.02 g (26.257 mmol) of hexane-2,5 dione in 15 ml of methanol. After dilution with 150 ml of ethyl acetate, the organic phase is washed twice with saturated sodium bicarbonate solution and once with saturated common salt solution. After being dried and spun in, the residue is chromatographed on silica gel (mobile solvent: ethyl acetate/hexane). 5.64 g (94%) of the desired compound is isolated.

MS (Cl) m/e (relative intensity) 230 (M$^+$, 100), 122 (10)

b) 1-[(1R)-Methyl-(2R)-fluoro-2-phenyl-eth-1-yl]-2,5-dimethyl-pyrrole 4.64 g (20.235 mmol) of [(1S)-phenyl-(2R)-(2,5-dimethylpyrrol-1-yl)]-propan-1 ol and 8.96 ml (60.705 mmol) of DBU are dissolved in 400 ml of toluene. After 9.19 g (30.392 mmol) of perfluorobutanesulfonic acid fluoride is added (slight heating to 30° C.), the batch is stirred for four hours at room temperature. The DBU is separated in the spherical separating funnel, and the organic phase is spun in until a dry state is reached. After chromatography on silica gel (mobile solvent: ethyl acetate/hexane), 2.96 g (63%) of the desired compound is obtained.

MS (Cl) m/e (relative intensity) 232 (M, 100), 212 (70.5), 122 (5.5)

c) (3R)-Fluoro-3-phenyl-prop-(2R)-yl-amine 2.96 g (12.797 mmol) of 1-[(1R)-methyl-(2R)-fluoro-2-phenyl-eth-1-yl]-2,5-dimethyl-pyrrole, 8.92 g (127.97 mmol) of hydroxylamine hydrochloride, 4.45 g (79.37 mmol) of potassium hydroxide, 64 ml of ethanol and 25 ml of water are refluxed overnight. The ethanol is spun off, and the residue is brought to pH 2 with 2 M hydrochloric acid. After being extracted four times with diethyl ether, the aqueous phase is brought to pH 9 with potassium hydroxide, and it is extracted three times with ethyl acetate. The combined ethyl acetate extracts are dried, and the solvent is spun off. 772.7 mg (39%) of the desired compound remains.

MS (Cl) m/e (relative intensity) 154 ($M^+$, 25.5), 145 (100)

d) (2R)-Methyl-3-oxo-6-[(3R)-fluoro-3-phenyl-prop-(2R)-yl-amino-methyl]-3,4-dihydro-2H-1,4-benzoxazine 1.02 g (6.658 mmol) of (3R)-fluoro-3-phenyl-prop-(2R)-yl-amine and 1.27 g (6.658 mmol) of (2R)-methyl-3-oxo-6-formyl-3,4-dihydro-2H-1,4-benzoxazine are dissolved in 25 ml of a mixture that consists of methanol and tetrahydrofuran (4:1). After being stirred overnight, 136 mg of sodium borohydride is added, and it is stirred for another two hours. The batch is added to water and extracted four times with ethyl acetate. The combined organic phases are washed with saturated sodium chloride solution, dried and spun in. After chromatography on silica gel (mobile solvent: ethyl acetate/hexane), 1.92 g (88%) of the desired compound is obtained.

MS (El) m/e (relative intensity) 219 (42.8), 176 (100)

e) (2R)-Methyl-3'-oxo-6-[(3R)-fluoro-3-phenyl prop-(2R)-yl-tert-butyloxycarbonyl-amino-methyl]-3,4-dihydro-2H-1,4-benzoxazine 1.92 g (5.847 mmol) of (2R)-methyl-3-oxo-6-[(3R)-fluoro-3-phenyl-prop-(2R)-yl-amino-methyl]-3,4-dihydro-2H-1,4-benzoxazine is stirred with 1.279 g (5.847 mmol) of di-tert-butyldicarbonate and 1.21 ml (8.705 mmol) of tri-ethylamine in 60 ml of dichloromethane overnight at room temperature. The batch is spun in until a dry state is reached, and the residue is chromatographed on silica gel (mobile solvent: ethyl acetate/hexane). 2.35 g (94%) of the desired compound is isolated.

MS (Cl) m/e (relative intensity) 429 ($M^+$, 15), 353 (40.5), 329 (52), 219 (46), 176 (100)

f) (2R)-Methyl-3-thioxo-6-[(3R)-fluoro-3-phenyl-prop-(2R)-yl-tert-butyloxycarbonyl-amino-methyl]-3,4-dihydro-2H-1,4-benzoxazine 2.35 g (5.485 mmol) of (2R)-methyl-3-oxo-6-[(3R)-fluoro-3-phenyl prop-(2R)-yl-tert-butyloxycarbonyl-amino-methyl]-3,4-dihydro-2H-1,4-benzoxazine is mixed in 230 ml of dimethoxy-ethane with 2.22 g of Lawesson's reagent and stirred for 65 hours at room temperature. The solvent is spun off, and the residue is chromatographed on silica gel (mobile solvent: ethyl acetate/hexane). 2.06 g (84%) of the desired compound is obtained.

MS (Cl) m/e (relative intensity) 445 ($M^+$, 25), 389 (100), 192 (44.5)

g) (2R)-Methyl-3'-amino-6-[(3R)-fluoro-3-phenyl prop-(2R)-yl-tert-butyloxycarbonyl-amino-methyl]-2H-1,4-benzoxazine 2.06 g (4.634 mmol) of (2R)-methyl-3-thioxo-6-[(3R)-fluoro-3-phenyl prop-(2R)-yl-tert-butyloxycarbonyl-amino-methyl]-3,4-dihydro-2H-1,4-benzoxazine is mixed with 40 ml of a 7 M solution of ammonia in methanol and stirred overnight at room temperature. After the batch is mixed with toluene, the solvent is spun off, and the residue is chromatographed on silica gel (mobile solvent: dichloromethane/isopropanol). 1.43 g (72%) of the desired compound is isolated.

MS (Cl) m/e (relative intensity) 428 ($M^+$, 100)

h) (2R)-Methyl-3-amino-6-[(3R)-fluoro-3-phenyl prop-(2R)-yl-amino-methyl]-2H-1,4-benzoxazine-dihydrochloride 1.43 g (3.345 mmol) of (2R)-methyl-3-amino-6-[(3R)-fluoro-3-phenyl prop-(2R)-yl-tert-butyloxycarbonyl-amino-methyl]-2H-1,4-benzoxazine is dissolved in 10 ml of dioxane and mixed with 10 ml of a 4 M solution of hydrochloric acid in dioxane. After stirring overnight, the batch is spun in until a dry state is reached, and the residue is absorptively precipitated with a mixture that consists of dichloromethane/methyl-tert-butyl ether. The crystalline product is suctioned off:

1.12 g (84%).

MS (Cl) m/e (relative intensity) 328 ($M^+$, 100), 308 (24.5), 218 (22), 175 (69)

Synthesis is carried analogously with use of the corresponding starting materials:

(2R)-Methyl-3-amino-6-[(3S)-fluoro-3-phenyl prop-(2S)-yl-amino-methyl]-2H-1,4-benzoxazine-dihydrochloride

EXAMPLE 5

(2R)-Methyl-3-amino-6-{[(1SR,3RS)-3-(trifluoromethyl)-cyclohexyl]-amino-methyl]}-2H-1,4-benzoxazine-dihydrochloride a) 3-(Trifluoromethyl)-cyclohexanon-oxime 5 g (30.095 mmol) of 3-(trifluoromethyl)-cyclohexanone is stirred in 30 ml of ethanol with 2.51 g (36.08 mmol) of hydroxylamine-hydrochloride, 3.95 g (48.081 mmol) of sodium acetate and 15.7 ml of water for six hours at 40° C. The mixture is diluted with water and shaken three times with ethyl acetate. The combined organic extracts are washed neutral, and the solvent is spun off after drying. The residue is chromatographed on silica gel (mobile solvent: ethyl acetate/hexane). 5.78 g (>100%) of the desired, still slightly contaminated compound is isolated.

MS (Cl) m/e (relative intensity) 182 ($M^+$, 100)

b) (1RS,3RS)- and (1SR,3RS)-3-Trifluoromethy-cyclohexylamine 5.28 g (29.142 mmol) of 3-(trifluoromethyl)-cyclohexanon-oxime is mixed in 200 ml of methanol with 7.71 ml of concentrated hydrochloric acid and 476.9 mg of Pd/C (10%) and hydrogenated overnight. The catalyst is suctioned off on a glass fiber filter, and the filtrate is spun in until a dry state is reached. The residue is taken up with 0.5N hydrochloric acid and extracted twice with methyl-tert-butyl ether. The aqueous phase is brought to pH 9 with potassium hydroxide, added to Extrelut and eluted with dichloromethane. The etuate is chromatographed after being spun in on silica get (mobile solvent: ethyl acetate/hexane). The two diastereomeric amines are obtained in each case as racemates.

MS (Cl) m/e (relative intensity) 224 (100), 208 (78), 182 (81), 168 (M+, 96.5)

c) (2R)-Methyl-3-oxo-6-{(E/Z)-[(1SR,3RS)-3-(trifluoromethyl)-cyclohexyl]-iminomethyl]}-3,4-dihydro-2H-1,4-benzoxazine 385.4 mg (2.016 mmol) of (1SR,3RS)-3-trifluoromethyl-cyclohexylamine, 337 mg (2.016 mmol) of (2R)-methyl-3-oxo-6-formyl-2H-3,4-dihydro-1,4-benzoxazine and 38 mg (0.2 mmol) of para-toluenesulfonic acid are boiled in 15 ml of benzene overnight in a water separator. The solid that is precipitated after the cooling is suctioned off and combined with the product that is obtained after chromatography of the residue (silica gel, ethyl acetate/hexane). The yield is 584.7 mg (85%).

MS (Cl) m/e (relative intensity) 341 (M+, 100)

d) (2R)-Methyl-3-oxo-6-{[(1SR,3RS)-3-(trifluoromethyl)-cyclohexyl]-amino-methyl]}-3,4-dihydro-2H-1,4-benzoxazine 360.6 mg (1.06 mmol) of (2R)-methyl-3'-oxo-6-{(E/Z)-[(1SR,3RS)-3-(trifluoromethyl)-cyclohexyl]-imino-methyl]}-3,4-dihydro-2H-1,4-benzoxazine is added in 11 ml of methanol and hydrogenated overnight with the addition of 0.29 ml of concentrated hydrochloric acid and 17.3 mg of Pd/C (10%).

The working-up is carried out as described in b). 165.9 mg (46%) of the desired compound is isolated.

MS (Cl) m/e (relative intensity) 343 (M+, 92), 176 (100)

e) (2R)-Methyl-3-oxo-6-{[(1SR,3RS)-3-(trifluoromethyl)-cyclohexyl]-tert-butyloxycarbonyl-amino-methyl]}-3,4-dihydro-2H-1,4-benzoxazine 166 mg (0.485 mmol) of (2R)-methyl-3-oxo-6-{[(1SR,3RS)-3-(trifluoromethyl)-cyclohexyl]-amino-methyl]}-3,4-dihydro-2H-1,4-benzoxazine is dissolved in 10 ml of dichloromethane, mixed with 0.1 ml (0.722 mmol) of triethylamine and 105.7 mg (0.485 mmol) of di-tert-butyldicarbonate and stirred overnight at room temperature. After being spun in until a dry state is reached, the residue is chromatographed as usual on silica gel (mobile solvent: ethyl acetate/hexane). 212.2 mg (99%) of the desired product remains.

MS (Cl) m/e (relative intensity) 443 (M+, 30.5), 386 (70.5), 343 (66), 176 (100)

f) (2R)-Methyl-3-thioxo-6-{[(1SR,3RS)-3-(trifluoromethyl)-cyclohexyl]-tert-butyloxycarbonyl-amino-methyl]}-3,4-dihydro-2H-1,4-benzoxazine 212 mg (0.480 mmol) of (2R)-methyl-3-oxo-6-{[(1SR,3RS)-3-(trifluoromethyl)-cyclohexyl]-tert-butyloxycarbonyl-amino-methyl]}-3,4-dihydro-2H-1,4-benzoxazine is mixed in 15 ml of dimethoxyethane with 194.8 mg of Lawesson's reagent and stirred overnight at room temperature. After the solvent is spun off, the residue is chromatographed on silica gel (mobile solvent: ethyl acetate/hexane). The desired compound is obtained in a 96% yield (210.9 mg).

MS (Cl) m/e (relative intensity) 459 (M+, 10), 403 (82), 359 (100), 192 (81)

g) (2R)-Methyl-3-amino-6-{[(1SR,3RS)-3-(trifluoromethyl)-cyclohexyl]-tert-butyloxycarbonyl-amino-methyl]}-2H-1,4-benzoxazine 210.9 mg of (2R)-methyl-3-thioxo-6-{[(1SR,3RS)-3-(trifluoromethyl)-cyclohexyl]-tert-butyloxycarbonyl-amino-methyl]}-3,4-dihydro-2H-1,4-benzoxazine is mixed with 10 ml of a 7 M solution of ammonia in methanol and stirred overnight at room temperature. After the batch is mixed with toluene, it is spun in until a dry state is reached, and the residue is chromatographed on silica gel (mobile solvent: ethyl acetate/hexane). 156.3 mg (77%) of the desired compound is obtained.

MS (Cl) m/e (relative intensity) 442 (M+, 100), 385 (40), 175 (22.5)

h) (2R)-Methyl-3-amino-6-{[(1SR,3RS)-3-(trifluoromethyl)-cyclohexyl]-amino-methyl]}-2H-1,4-benzoxazine-dihydrochloride 156.3 mg (0.354 mmol) of (2R)-methyl-3-amino-6-{[(1SR,3RS)-3-(trifluoromethyl)-cyclohexyl]-tert-butyloxycarbonyl-amino-methyl]}-2H-1,4-benzoxazine is dissolved in one ml of dioxane and mixed with 2 ml of a 4 M solution of hydrochloric acid in dioxane. After stirring overnight, it is evaporated to the dry state, and the residue is absorptively precipitated with 10 ml of a mixture that consists of dichloromethane and methyl-tert-butyl-ether (1:1). The precipitated product is suctioned off and dried at the oil pump. The yield is 101.2 mg (69%).

MS (Cl) m/e (relative intensity) 342 (M+, 78), 175 (100)

Synthesized analogously are:

(2R)-Methyl-3'-amino-6-{[(1RS,3RS)-3-(trifluoromethyl)-cyclohexyl]-amino-methyl]}-2H-1,4-benzoxazine-dihydrochloride (2R)-methyl-3-amino-6-{[(1SR,2RS)-2-(trifluoromethyl)-cyclohexyl]-amino-methyl]}-2H-1,4-benzoxazine-dihydrochloride (2R)-methyl-3-amino-6-{[(1RS,2RS)-2-(trifluoromethyl)-cyclohexyl]-amino-methyl]}-2H-1,4-benzoxazine-dihydrochloride

What is claimed is:

1. Compounds 3f formula I, their tautomeric and isomeric forms and salts

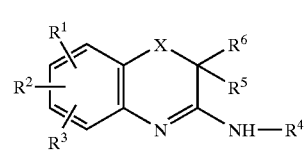

(I)

in which

X is O,

R$^1$ is —(CHR$^9$)$_n$—NR$^7$-A-NR$^8$—B or —(CHR$^9$)$_n$—NR$^7$—B,

R$^2$ is hydrogen

R$^3$ is hydrogen, halogen, NO$^2$, cyano, CF$^3$, —OCF$^3$, —S—R$^9$, —O—R$^9$, C$^{3-7}$cycloalkyl, —NR$^9$—C(=NR$^{10}$)—R$^{11}$, —NH—CS—NR$^{12}$R$^{13}$, NH—CO—NR$^{12}$R$^{13}$, —SO$_2$NR$^{12}$R$^{13}$, —CO—NR$^{12}$R$^{13}$, —CO—R$^{14}$, NR$^{15}$R$^{16}$, C$_{6-10}$-aryl, which optionally is substituted with halogen, cyano, C$^{1-4}$-alkyl, —S—R$^9$, or —O—R$^9$, 5- or 6-membered heteroaryl with 1 to 4 oxygen, sulfur or nitrogen atoms, C$_{1-6}$-alkyl, which optionally is substituted with halogen, —OR$^9$, —SR$^9$, —NR$^{12}$R$^{13}$, =NR$^{12}$, =NOC$^{1-6}$-alkyl, =N—NHaryl, phenyl, C$^{3-7}$-cycloalkyl or 5- or 6-membered heteroaryl, C$_{2-6}$-alkenyl, which optionally is substituted with halogen, CONH$^2$, C=N or phenyl, C$_{2-6}$-alkinyl, which optionally is substituted with halogen, CONH$^2$, C=N or phenyl, R$^4$ is hydrogen or acyl, R$^5$ and R$^6$, are independently hydrogen, C$_{3-7}$-cycloalkyl, phenyl, C$_{1-6}$-alkyl, C$_{2-6}$-alkenyl or C$_{2-6}$-alkynyl radicals, which can be substituted in each case with halogen, OH, O—C$_{1-6}$-alkyl, SH, S—C$_{1-6}$-alkyl, NR$^{15}$R$^{16}$, 5- or 6-membered heteroaryl with 1–3 N, O or S atoms, phenyl or C$_{3-7}$-cycloalkyl, R$^7$ is hydrogen, C$_{1-6}$-alkyl, which can be substituted with phenyl, COOC$_{1-6}$-alkyl or COC$_{1-6}$-alkyl, $R^8$ is hydrogen, A is straight-chain or branched —$C_{1-6}$-alkylene, straight-chain or branched —$C_{2-6}$-alkenylene, B is halogenated $C_{1-8}$-alkyl, which can be substituted with —$NHR^7$ or with $C_{6-10}$-aryl, whereby the aryl radical can be substituted with halogen, cyano, OH, $C_{1-4}$-alkoxy, $C_{1-4}$-alkyl, $CF_3$ and —$OCF_3$; $C_{3-8}$-alkinyl, which can be substituted with $C_{6-10}$-aryl; —$(CH_2)_p$—$C_{6-10}$-aryl, which is substituted with —$OCF_3$; or $C_{3-7}$-cycloalkyl, which is substituted with $CF_3$, n is 0, 1 to 6, p is 0 to 6, $R^9$ and $R^{10}$ are hydrogen or $C_{1-4}$-alkyl, $R^{11}$ is $C_{1-6}$-alkyl, —$NH_2$, —NH—$CH_3$, —NH—CN, $C_{6-10}$-aryl that is optionally substituted with halogen, $C_{1-4}$-alkyl or $CF_3$; or 5- or 6-membered heteroaryl with 1 to 4 nitrogen, sulfur or oxygen atoms that is optionally substituted with halogen, $C_{1-4}$-alkyl or $CF_3$, $R^{12}$ and $R^{13}$ are hydrogen, $C_{1-6}$-alkyl; phenyl that is optionally substituted with halogen or $C_{1-4}$-alkyl; benzyl that is optionally substituted with halogen or $C_{1-4}$-alkyl, or $C_{3-7}$-cycloalkyl, $R^{14}$ is hydrogen, hydroxy, $C_{1-6}$-alkoxy, phenyl; $C_{1-6}$-alkyl that is optionally substituted with $CO_2H$, $CO_2C_{1-6}$-alkyl, hydroxy, $C_{1-4}$-alkoxy, halogen, $NR^{15}R^{16}$, $CONR^{12}R^{13}$, or phenyl; or $C_{2-6}$-alkenyl that is optionally substituted with phenyl, cyano, $CONR^{12}R^{13}$ or $CO_2C_{1-4}$-alkyl, $R^{15}$ and $R^{16}$ are hydrogen, $C_{1-6}$-alkyl; phenyl that is optionally substituted with halogen or $C_{1-4}$-alkyl; or benzyl that is optionally substituted with halogen or $C_{1-4}$-alkyl, or $R^{15}$ and $R^{16}$ together with the nitrogen atom form a saturated 5-, 6-, or 7-membered ring, which can contain another nitrogen, oxygen or sulfur atom and can be substituted with $C_{1-4}$-alkyl, or a phenyl, benzyl or benzoyl radical that is optionally substituted with halogen.

2. Compounds according to claim 1, in which $R^6$ is hydrogen.

3. Compounds according to claim 1 in which $R^5$ is $C_{1-6}$-alkyl.

4. Compounds according to claim 1 in which $R^4$ is hydrogen.

5. Compounds according to claim 1 in which $R^3$ is hydrogen.

6. Compounds according to claim 1, in which A is straight-chain or branched $C_{1-6}$-alkylene.

7.
(2R)-Methyl-3-amino-6-(2,2,3,3,3-pentafluoropropylamino-methyl)-2H-1,4-benzoxazine-dihydrochloride (2R)-Methyl-3-amino-6-(4,4,4-trifluorobutylamino-methyl)-2H-1,4-benzoxazine-dihydrochloride (2R)-methyl-3-amino-6-[4,4,4-trifluorobut-(2RS)-yl-amino-methyl]-2H-1,4-benzoxazine-dihydrochloride (2R)-methyl-3-amino-6-[(3R)-fluoro-3-phenyl-prop-(2R)-yl-amino-methyl]-2H-1,4-benzoxazine-dihydrochloride.

8. A pharmaceutical composition comprising a compound according to claim 1 and one or more pharmaceutically acceptable vehicles or adjuvants.

9. A process for the production of a compound of claim 1, wherein (a) a compound of formula IIa or IIb or a salt thereof is reacted with ammonia, and (b) the isomers are separated or the salts formed, wherein existing amino groups are optionally intermediately protected and optionally then acylated

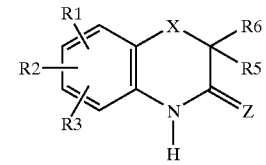

IIa

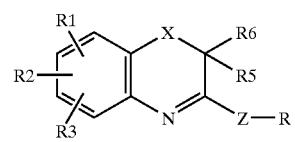

IIb wherein
$R^1$, $R^2$, $R^3$, $R^5$, $R^6$ and X are as defined in claim 1, Z is oxygen or sulfur and R means $C_{1-6}$-alkyl.

10. A compound of formula IIa or IIb or salts thereof

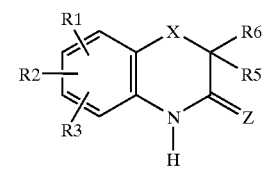

IIa

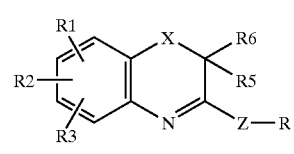

IIb wherein
X is O, $R^1$ is —$(CHR^9)_n$—$NR^7$-A-$NR^8$—B or —$(CHR^9)_n$—$NR^7$—B, $R^2$ is hydrogen $R^3$ is hydrogen, halogen. $NO_2$, cyano, $CF_3$, —$OCF_3$, —S—$R^9$, —O—$R^9$, $C_{3-7}$-cycloalkyl, $NR^9$—C(=$NR^{10}$)—$R^{11}$, —NH—CS—$NR^{12}R^{13}$, NH—CO—$NR^{12}R^{13}$, —$SO_2NR^{12}R^{13}$, —CO—$NR^{12}R^{13}$, —CO—$R^{14}$, $NR^{15}R^{16}$, $C_{6-10}$-aryl, which optionally is substituted with halogen, cyano, $C_{1-4}$-alkyl, —S—$R^9$, or —O—$R^9$, 5- or 6-membered heteroaryl with 1 to 4 oxygen, sulfur or nitrogen atoms, $C_{1-6}$-alkyl, which optionally is substituted with halogen, —$OR^9$, —$SR^9$, —$NR^{12}R^{13}$, =$NR^{12}$, =$NOC_{1-6}$-alkyl, =N-NHaryl, phenyl, $C_{3-7}$-cycloalkyl or 5- or 6-membered heteroaryl, $C_{2-6}$-alkenyl, which optionally is substituted with halogen, $CONH_2$, C=N or phenyl, $C_{2-6}$-alkinyl, which optionally is substituted with halogen, $CONH_2$, C=N or phenyl, $R^5$ and $R^6$, are independently hydrogen, $C_{3-7}$-cycloalkyl, phenyl, $C_{1-6}$-alkyl, $C_{2-6}$-alkenyl or $C_{2-6}$-alkynyl radicals, which can be substituted in each case with halogen, OH, O—$C_{1-6}$-alkyl, SH, S—$C_{1-6}$-alkyl, $NR^{15}R^{16}$, 5- or 6-membered heteroaryl with 1–3 N, O or S atoms, phenyl or $C_{3-7}$-cycloalkyl, Z is oxygen or sulfur, and R means $C_{1-4}$-alkyl.

* * * * *